United States Patent [19]

Yamada et al.

[11] Patent Number: 6,002,044
[45] Date of Patent: Dec. 14, 1999

[54] PRODUCTION METHOD OF BORATE COMPOUNDS

[75] Inventors: Morihiko Yamada; Tsuyoshi Katoh, both of Kawasaki; Norihide Arai, Oita, all of Japan

[73] Assignee: Showa Denko K.K., Tokyo, Japan

[21] Appl. No.: 09/188,888

[22] Filed: Nov. 10, 1998

Related U.S. Application Data

[60] Provisional application No. 60/076,058, Feb. 26, 1998.

[30] Foreign Application Priority Data

Nov. 12, 1997 [JP] Japan ................................ 9-310926

[51] Int. Cl.$^6$ ..................................... C07F 5/02
[52] U.S. Cl. ...................... 564/8; 568/2; 568/6; 568/1; 546/13
[58] Field of Search ................. 568/1, 2, 6; 546/13; 564/8

[56] References Cited

U.S. PATENT DOCUMENTS

| 3,332,962 | 7/1967 | Grayson | 549/6 |
| 4,136,102 | 1/1979 | Crivello | 556/20 |
| 5,468,902 | 11/1995 | Castellanos | 568/6 |
| 5,500,453 | 3/1996 | Toba | 522/25 |
| 5,585,507 | 12/1996 | Nakano | 556/7 |
| 5,668,192 | 9/1997 | Castellanos | 552/31 |

FOREIGN PATENT DOCUMENTS

| 555058 | 8/1993 | European Pat. Off. | C07F 5/02 |

OTHER PUBLICATIONS

CA:127:50785 abs of JP 09110878, Oct. 1995.
CA:127:50786 abs of JP09110879, Oct. 1995.
CA:127:206408 abs of JP09194816, Jan. 1996.

*Primary Examiner*—Paul J. Killos
*Assistant Examiner*—Jean F Vollano
*Attorney, Agent, or Firm*—Sughrue, Mion, Zinn, Macpeak & Seas, PLLC

[57] ABSTRACT

A method for producing a borate compound represented by formula (1) is disclosed, comprising a first step of reacting lithium or magnesium or a compound containing lithium or magnesium, a halide represented by formula (2) and a compound represented by formula (3) in a solvent to produce a boronate compound precursor, a second step of reacting lithium or magnesium or a compound containing lithium or magnesium, a halide represented by formula (4) and the boronate compound precursor obtained in the first step in a solvent to produce a borate metal salt, and a third step of adding an onium halide represented by formula (5) to the borate metal salt obtained in the second step to effect ion-exchange reaction (the formulae are as described in the specification).

10 Claims, No Drawings

PRODUCTION METHOD OF BORATE COMPOUNDS

CROSS REFERENCE TO RELATED APPLICATIONS

This application is an application filed under 35 U.S.C. §111(a) claiming benefit pursuant to 35 U.S.C. 0119(e)(1) of the filing date of the Provisional Application 60/076,058, filed Feb. 26, 1998, pursuant to 35 U.S.C. §111(b).

FIELD OF THE INVENTION

The present invention relates to a production method of borate compounds, more specifically, the present invention relates to a production method of borate compounds useful as a photopolymerization initiator or a photoabsorptive decolorizer.

BACKGROUND OF THE INVENTION

With respect to the production method of tetramethylammonium methyltriphenylborate as one of borate compounds represented by formula (1) shown later, a method of ion-exchanging lithium methyltriphenylborate obtained from triphenylborane and methyllithium by tetramethylammonium bromide is commonly known [see, for example, Journal of American Chemical Society, Vol. 107, pp. 6710–6711 (1985)].

With respect to the production method of triphenylborane, a method of reacting metallic magnesium, boron trifluoride diethyl etherate and phenyl bromide in diethyl ether is commonly known [see, for example, Journal of Organic Chemistry, Vol. 51, pp. 427–432 (1986)].

More specifically, in the case of the tetramethylammonium methyltriphenylborate, phenyl bromide is reacted with metallic magnesium in diethyl ether to prepare a Grignard reagent, the reagent is added dropwise to a solution containing boron trifluoride diethyl etherate dissolved in diethyl ether, the mixed solution is stirred for several hours to obtain triphenylborane, the triphenylborane obtained is added to methyllithium without passing through isolation to form lithium methyltriphenylborate, and tetramethylammonium bromide is added thereto to effect ion exchanging, as a result, tetramethylammonium methyltriphenylborate is obtained.

With respect to the production method of alkyldiaryl boronate (or aryldialkyl boronate), a method of reacting a boric acid ester with a Grignard reagent or organic lithium in diethyl ether is commonly known [see, for example, Organometallics, pp. 1058–1067 (1993)].

In these conventional production methods, the solvent used for the Grignard reaction or reaction of triarylborane or trialkylborane is restricted to diethyl ether in view of the problem of side reaction [see, for example, Journal of Organic Chemistry, Vol. 51, pp. 427–432 (1986)].

The Grignard reaction in general is, however, easy to occur in tetrahydrofuran rather than in diethyl ether [see, for example, Teruaki Mukaiyama (compiler), Kiso Yuki Kagaku (Basic Organic Chemistry), Maruzen, page 79] and in the case of halides difficult to cause the Grignard reaction in diethyl ether, the final yield of the borate compound disadvantageously decreases.

SUMMARY OF THE INVENTION

The object of the present invention is to solve these problems in conventional production methods and provide a production method capable of obtaining a high-purity borate compound useful as a photopolymerization initiator or photoabsorptive decolorizer in a high yield.

As a result of extensive investigations on these problems, the present inventors have found that the above-described object can be attained by performing the reaction using specific starting materials, a specific reaction solvent and a specific reaction process. The present invention has been accomplished based on this finding.

More specifically, the present invention provides:

1) A method for producing a borate compound represented by formula (1), comprising:
   a first step of reacting lithium or magnesium or a compound containing lithium or magnesium, a halide represented by formula (2) and a compound represented by formula (3) in a solvent to produce a boronate compound precursor;
   a second step of reacting lithium or magnesium or a compound containing lithium or magnesium, a halide represented by formula (4) and the boronate compound precursor obtained in the first step in a solvent to produce a borate metal salt; and
   a third step of adding an onium halide represented by formula (5) to the borate metal salt obtained in the second step to effect ion-exchange reaction:

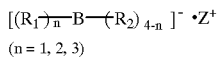

(1)

$[(R_1)_n\text{—}B\text{—}(R_2)_{4-n}]^- \cdot Z^+$ $(n = 1, 2, 3)$ (wherein $R_1$ and $R_2$ are different from each other and $R_1$ and $R_2$ each independently represents an alkyl group, an alkenyl group, an aryl group, an aralkyl group, a heterocyclic group or an alicyclic group, and $Z^+$ represents an ammonium cation, a sulfonium cation, an oxosulfonium cation, a pyridinium cation, a phosphonium cation or an iodonium cation);

$R_1\text{—}Y_1$ (2)

(wherein $R_1$ is the same as $R_1$ in formula (1), and $Y_1$ represents a halogen atom);

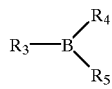

(3)

(wherein $R_3$, $R_4$ and $R_5$, which may be the same or different, each represents an alkyloxy group, an alkenyloxy group, an aryloxy group, an aralkyloxy group or a halogen atom and when $R_4$ and $R_5$ are an alkyloxy group, an alkenyloxy group, an aryloxy group or an aralkyloxy group, $R_4$ and $R_5$ may be combined to each other to form a cyclic structure together with the boron atom);

$R_2\text{—}Y_2$ (4)

(wherein $R_2$ is the same as $R_2$ in formula (1), and $Y_2$ represents a halogen atom);

$Z^+ \cdot X^-$ (5)

(wherein $Z^+$ is the same as $Z^-$ in formula (1), and X represents a halogen atom);

2) The method for producing a borate compound as described in 1) above, wherein in the first step, the boronate compound precursor is produced by:
   (A) reacting lithium or magnesium or a compound containing lithium or magnesium with a halide represented by formula (2) in a solvent and adding thereto and reacting therewith a compound represented by formula (3);
   (B) adding a reaction product of lithium or magnesium or a compound containing lithium or magnesium with a halide represented by formula (2) reacted in a solvent to a compound represented by formula (3) to react therewith;
   (C) simultaneously adding a reaction product of lithium or magnesium or a compound containing lithium or magnesium with a halide represented by formula (2) reacted in a solvent, and a compound represented by formula (3) to react with each other; or
   (D) reacting lithium or magnesium or a compound containing lithium or magnesium with a halide represented by formula (2) in a solvent in the presence of a compound represented by formula (3);
3) The method for producing a borate compound as described in 1) or 2) above, wherein in the second step, the borate metal salt is produced by:
   (E) reacting lithium or magnesium or a compound containing lithium or magnesium with a halide represented by formula (4) and adding thereto and reacting therewith the boronate compound precursor obtained in the first step;
   (F) adding a reaction product of lithium or magnesium or a compound containing lithium or magnesium with a halide represented by formula (4) reacted in a solvent to the boronate compound precursor obtained in the first step to react therewith;
   (G) simultaneously adding a reaction product of lithium or magnesium or a compound containing lithium or magnesium with a halide represented by formula (4) reacted in a solvent, and the boronate compound precursor obtained in the first step to react with each other; or
   (H) reacting lithium or magnesium or a compound containing lithium or magnesium with a halide represented by formula (4) in a solvent in the presence of the boronate compound precursor obtained in the first step;
4) The method for producing a borate compound as described in 1) to 3) above, wherein the lithium or magnesium or compound containing lithium or magnesium used in the first step is metallic lithium, metallic magnesium or an organic lithium compound;
5) The method for producing a borate compound as described in 1) to 4) above, wherein the lithium or magnesium or compound containing lithium or magnesium used in the second step is metallic lithium, metallic magnesium or an organic lithium compound;
6) The method for producing a borate compound as described in 1) to 5) above, wherein the first step and the second step are continuously performed in the same reaction vessel;
7) The method for producing a borate compound as described in 6) above, wherein the lithium or magnesium or compound containing lithium or magnesium used in the first step and the second step is metallic magnesium and the metallic magnesium for use in the second step is added simultaneously with the metallic magnesium for use in the first step;
8) The method for producing a borate compound as described in 1) to 7) above, wherein the compound represented by formula (3) used in the first step is trialkyl borate;
9) The method for producing a borate compound as described in 1) to 8) above, wherein the solvent used in the second step is tetrahydrofuran; and
10) The method for producing a borate compound as described in 1) to 9) above, wherein the halide represented by formula (2) used in the first step is a halide where $R_1$ is an α-naphthyl group which may have a substituent or a β-naphthyl group which may have a substituent.

DETAILED DESCRIPTION OF THE INVENTION

The alkyl group represented by $R_1$ or $R_2$ in formula (1) for the borate compound produced by the production method of a borate compound according to the present invention may have a substituent and specifically, the alkyl group is preferably a substituted or unsubstituted, linear or branched alkyl group having from 1 to 10 carbon atoms. Examples thereof include methyl, ethyl, propyl, isopropyl, butyl, isobutyl, sec-butyl, pentyl, hexyl, heptyl, octyl, 3-methoxypropyl, 4-chlorobutyl and 2-diethylaminoethyl.

The alkenyl group represented by $R_1$ or $R_2$ in formula (1) may have a substituent and specifically, the alkenyl group is preferably a substituted or unsubstituted, linear or branched alkenyl group having from 2 to 12 carbon atoms. Examples thereof include a vinyl group, a propenyl group, a butenyl group, a pentenyl group, a hexenyl group, a heptenyl group, an octenyl group, a dodecenyl group and a prenyl group.

The aryl group represented by $R_1$ or $R_2$ in formula (1) may have a substituent and specifically, the aryl group is a substituted or unsubstituted aryl group. Examples thereof include phenyl, tolyl, xylyl, 4-ethylphenyl, 4-butylphenyl, 4-tert-butylphenyl, 4-methoxyphenyl, 4-diethylaminophenyl, 2-methoxyphenyl, 1-naphthyl, 2-naphthyl, 6-methoxy-2-naphthyl, 4-methyl-1-naphthyl, anthranyl, phenanthryl and pyrenyl.

The aralkyl group represented by $R_1$ or $R_2$ in formula (1) may have a substituent and specifically, the aralkyl group is a substituted or unsubstituted aralkyl group. Examples thereof include a benzyl group, a phenethyl group, a propiophenyl group, a 1-naphthylmethyl group, a 2-naphthylmethyl group and a 4-methoxybenzyl group.

The heterocyclic group represented by $R_1$ or $R_2$ in formula (1) may have a substituent and specifically, the heterocyclic group is a substituted or unsubstituted heterocyclic group. Examples thereof include a pyridyl group, a quinolyl group, a methylpyridyl group and an indolyl group.

The alicyclic group represented by $R_1$ or $R_2$ in formula (1) may have a substituent and specifically, the alicyclic group is a substituted or unsubstituted alicyclic group. Examples thereof include a cyclohexyl group, a 4-methylcyclohexyl group, a cyclopentyl group and a cycloheptyl group.

Specific examples of the ammonium cation represented by $Z^+$ in formula (1) include tetramethylammonium cation, tetraethylammonium cation, tetrapropylammonium cation, tetra-n-butylammonium cation, tetra-n-pentylammonium cation, tetra-n-octylammonium cation, tetrabenzylammonium cation, tetraphenylammonium cation, tetracyclohexylammonium cation, triphenylphenacylammonium cation, triphenyl(4-aminophenyl)ammonium cation.

Specific examples of the sulfonium cation represented by $Z^+$ in formula (1) include dimethyl-tert-butylsulfonium cation, dimethylbenzylsulfonium cation, dimethyl(4-chlorobenzyl)sulfonium cation, dibutyl(4-bromobenzyl)sulfonium cation, dimethyl(4-cyanobenzyl)sulfonium cation, dimethylphenacylsulfonium cation, methyl(dimethylaminomethyl)(4-tolyl)sulfonium cation, triphenylsulfonium cation and 4-methoxyphenyldiphenylsulfonium cation.

Specific examples of the oxosulfonium cation represented by $Z^+$ in formula (1) include dimethyl-tert-butyloxosulfonium cation, dimethylbenzyloxosulfonium cation, dimethyl(4-chlorobenzyl)oxosulfonium cation, dibutyl(4-bromobenzyl)oxosulfonium cation, dimethyl(4-cyanobenzyl)-oxosulfonium cation, dimethylphenacyloxosulfonium cation, methyl(dimethylaminomethyl)(4-tolyl)oxosulfonium cation, triphenyloxosulfonium cation and 4-methoxyphenyldiphenyloxosulfonium cation.

Specific examples of the phosphonium cation represented by $Z^+$ in formula (1) include tetramethylphosphonium cation, tetraethylphosphonium cation, tetrapropylphosphonium cation, tetra-n-butylphosphonium cation, tetra-n-pentylphosphonium cation, tetra-n-octylphosphonium cation, tetrabenzylphosphonium cation, tetraphenylphosphonium cation, tetracyclohexylphosphonium cation, triphenylphenacylphosphonium cation and triphenyl(4-aminophenyl)phosphonium cation.

Specific examples of the iodonium cation represented by $Z^+$ in formula (1) include diphenyliodonium cation, 4-butoxyphenyl(4'-methylphenyl)iodonium cation, bis(4-aminophenyl)iodonium cation and 4,4'-bis-tert-butylphenyliodonium cation.

Specific examples of the pyridinium cation represented by $Z^+$ in formula (1) include N-methylpyridinium cation and N-butylpyridinium cation.

Specific examples of the borate compound represented formula (1) include tetramethylammonium ethyltributylborate, tetra-n-butylammonium phenethyltrimethylborate, tetraethylammonium phenyltriisobutylborate, tetra-n-butylammonium phenethyltri(4-methylphenyl)borate, tetramethylammonium ethyltriphenylborate, tetra-n-butylammonium phenethyltri(4-methylphenyl)borate, tetraethylammonium n-octyltri(4,5-diethylphenyl)borate, tetra-n-butylammonium n-pentyltri(4-methoxyphenyl)borate, tetra-n-octylammonium n-butyltri(4-naphthyl)borate, tetra-n-octylammonium n-butyltri(1-naphthyl)borate, tetra-n-butylammonium n-butyltri(2-naphthyl)borate, tetra-n-butylammonium n-butyltri(6-methoxy2-naphthyl)borate, tetra-n-butylammonium n-butyltri(4-methyl-1-naphthyl)borate, tetraethylammonium n-octyltri(4,5-diethylnaphthyl)borate, tetra-n-butylammonium ethyltriacenaphthylborate, tetra-n-butylammonium tri-n-butylpyrenylborate, tetra-n-butylammonium di-n-butyldianthranylborate, N-methylpyridinium n-butyltriphenylborate, triphenylsulfonium n-butyltri(1-naphthyl)borate, triphenyloxosulfonium n-butyltri(1-naphthyl)borate, tetra-n-butylphosphonium n-butyltriphenylborate and diphenyliodonium n-butyltriphenylborate.

Specific examples of the compound represented by formula (2) include methyl bromide, ethyl chloride, propyl chloride, isopropyl chloride, butyl chloride, isobutyl bromide, pentyl bromide, hexyl bromide, octyl chloride, 3-methoxypropyl bromide, vinyl bromide, propenyl bromide, butenyl bromide, pentenyl bromide, hexenyl bromide, heptenyl bromide, octenyl bromide, bromobenzene, iodobenzene, bromotoluene, bromoxylene, 1-bromo-4-ethylbenzene, 1-bromo-4-butylbenzene, 1-bromo-4-tert-butylbenzene, 1-bromo-4-methoxybenzene, 1-bromo-4-diethylaminobenzene, 1-bromo-2-methoxybenzene, 1-bromonaphthalene, 1-bromo-4-methylnaphthalene, benzyl chloride, phenethyl bromide, 1-bromo-3-phenylpropane, 1-(bromomethyl)naphthalene, 2-(bromomethyl)naphthalene, 2-bromo-6-methoxynaphthalene, 4-methoxybenzyl chloride, cyclohexyl chloride and 1-chloro-4-methylcyclohexane.

The alkyloxy group represented by $R_3$, $R_4$ or $R_5$ in formula (3) may have a substituent and specifically, the alkyloxy group is preferably a substituted or unsubstituted, linear or branched alkyloxy group having from 1 to 10 carbon atoms. Examples thereof include methoxy, ethoxy, propoxy, isopropoxy, butoxy, isobutoxy, sec-butoxy, pentyloxy, hexyloxy, heptyloxy, octyloxy, 3-methoxypropoxy, 4-chlorobutoxy and 2-diethylaminoethoxy.

The alkenyloxy group represented by $R_3$, $R_4$ or $R_5$ in formula (3) may have a substituent and specifically, the alkenyloxy group is preferably a substituted or unsubstituted, linear or branched alkenyloxy group having from 3 to 12 carbon atoms. Examples thereof include a propenyloxy group, a butenyloxy group, a pentenyloxy group, a hexenyloxy group, a heptenyloxy group, an octenyloxy group, a dodecenyloxy group and prenyloxy group.

The aryloxy group represented by $R_3$, $R_4$ or $R_5$ in formula (3) may have a substituent and specifically, the aryloxy group is a substituted or unsubstituted aryloxy group. Examples thereof include phenoxy, tolyloxy, xylyloxy, 4-ethylphenoxy, 4-butylphenoxy, 4-tert-butylphenoxy, 4-methoxyphenoxy, 4-diethylaminophenoxy, 2-methylphenoxy, 2-methoxyphenoxy, 1-naphthoxy, 2-naphthoxy and 4-methylnaphthoxy.

The aralkyloxy group represented by $R_3$, $R_4$ or $R_5$ in formula (3) may have a substituent and specifically, the aralkyloxy group is a substituted or unsubstituted aralkyloxy group. Examples thereof include a benzyloxy group, a phenethyloxy group, a phenylpropyloxy group, a 1-naphthylmethyloxy group, a 2-naphthylmethyloxy group and a 4-methoxybenzyloxy group.

Specific examples of the compound represented by formula (3) include a trimethyl borate, a triethyl borate, a tri-n-propyl borate, a truisopropyl borate, a tri-n-butyl borate, a truisobutyl borate, a tri-n-octyl borate, a butyldiethyl borate, an ethyldi(2-phenethyl) borate, a triphenyl borate, a diethyl-4-methoxyphenyl borate, a diethylcyclohexyl borate, trichloroborane, trifluoroborane, diethoxychloroborane and n-butoxydichloroborane.

Specific examples of the compound having a cyclic structure containing a boron atom and two oxygen atoms within the ring formed by combining $R_4$ and $R_5$ in formula (3) to each other include 2-methoxy-1,3,2-dioxaborinane, 2-ethoxy-1,3,2-dioxaborolane, 2-butoxy-1,3,2-dioxaborinane, 2phenoxy-1,3,2-dioxaborinane, 2-phenoxy-4,4,6-trimethyl1,3,2-dioxaborinane, 2-naphthoxy-1,3,2-dioxaborinane, 2-methoxy-1,3,2-benzodioxaborole and 2-ethoxy-1,3,2-benzodioxaborin.

Specific examples of the compound represented by formula (4) include methyl bromide, ethyl chloride, propyl chloride, isopropyl chloride, butyl chloride, isobutyl bromide, pentyl bromide, hexyl bromide, octyl chloride, 3-methoxypropyl bromide, vinyl bromide, propenyl bromide, butenyl bromide, pentenyl bromide, hexenyl bromide, heptenyl bromide, octenyl bromide, bromobenzene, iodobenzene, bromotoluene, bromoxylene, 1-bromo-4-ethylbenzene, 1-bromo-4-butylbenzene, 1-bromo-4-tert-butylbenzene, 1-bromo-4-methoxybenzene, 1-bromo-4-diethylaminobenzene, 1-bromo-2-methoxybenzene, 1-bromonaphthalene, 1-bromo-4-methylnaphthalene, benzyl chloride, phenethyl bromide, 1-bromo-3-phenylpropane, 1-(bromomethyl)naphthalene, 2-(bromomethyl)naphthalene, 2-bromo-6-methoxynaphthalene, 4-methoxybenzyl chloride, cyclohexyl chloride and 1-chloro-4-methylcyclohexane.

Specific examples of the onium halide represented by formula (5) include tetramethylammonium bromide, tetraethylammonium bromide, tetrapropylammonium iodide, tetra-n-butylammonium bromide, tetra-n-pentylammonium chloride, tetra-n-octylammonium bromide, tetrabenzylammonium bromide, tetraphenylammonium bromide, tetracyclohexylammonium bromide, N-methylpyridinium chloride, N-butylpyridinium bromide, dimethyl-tert-butylsulfonium bromide, dimethylbenzylsulfonium bromide, dimethyl(4-chlorobenzyl)sulfonium bromide, dibutyl(4-bromobenzyl)sulfonium chloride, dimethyl(4-cyanobenzyl)sulfonium bromide, dimethylphenacylsulfonium chloride, methyl (dimethylaminomethyl)(4-tolyl)sulfonium bromide, triphenylsulfonium chloride, 4-methoxyphenyldiphenylsulfonium bromide, dimethyl-tert-butyloxosulfonium bromide, dimethylbenzyloxosulfonium bromide, dimethyl(4-chlorobenzyl)oxosulfonium chloride, dibutyl(4-bromobenzyl)oxosulfonium chloride, dimethyl(4-cyanobenzyl)oxosulfonium chloride, dimethylphenacyloxosulfonium chloride, methyl(dimethylaminomethyl)(4-tolyl)oxosulfonium chloride, triphenyloxosulfonium chloride, 4-methoxyphenyldiphenyloxosulfonium iodide, tetramethylphosphonium chloride, tetraethylphosphonium chloride, tetrapropylphosphonium chloride, tetra-n-butylphosphonium bromide, tetra-n-pentylphosphonium bromide, tetra-n-octylphosphonium chloride, tetrabenzylphosphonium chloride, tetraphenylphosphonium iodide, tetracyclohexylphosphonium bromide, tetraphenylphosphonium bromide, triphenylphenacylphosphonium chloride, triphenyl(4-aminophenyl)phosphonium bromide, diphenyliodonium chloride, 4-butoxyphenyl(4-methylphenyl)iodonium chloride and bis(4-aminophenyl)iodonium chloride and bis-(4-tert-bytylphenol)iodonium chloride.

The boronate compound precursor produced in the first step of the present invention by reacting lithium or magnesium or a compound containing lithium or magnesium, a halide represented by formula (2) and a compound represented by formula (3) is presumed to be the compound represented by the following formula (6) and/or formula (7) and/or formula (8):

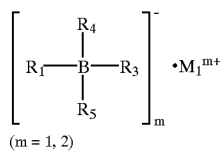
(m = 1, 2)

(wherein $R_1$ is the same as $R_1$ in formula (1), $R_3$, $R_4$ and $R_5$ are the same as $R_3$, $R_4$ and $R_5$ in formula (3), respectively, and $M_1$ represents a lithium atom or a magnesium atom);

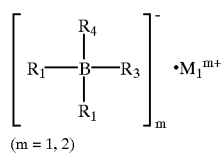
(m = 1, 2)

(wherein $R_1$ is the same as $R_1$ in formula (1), $R_3$ and $R_4$ are the same as $R_3$ and $R_4$ in formula (3), respectively, and $M_1$ represents a lithium atom or a magnesium atom);

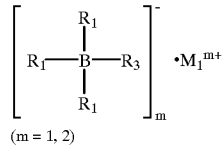
(m = 1, 2)

(wherein $R_1$ is the same as $R_1$ in formula (1), $R_3$ is the same as $R_3$ in formula (3), and $M_1$ represents a lithium atom or a magnesium atom).

Specific examples of the boronate compound precursors represented by formulae (6) to (8) include lithium ethyltriethoxyborate, lithium phenethyltriisopropoxyborate, lithium phenyltri-n-butoxyborate, lithium phenethyltriethoxyborate, magnesium bis(ethyltriisopropoxyborate), magnesium bis(phenethyltriethoxyborate), magnesium bis(noctyltri-n-butoxyborate), magnesium bis(n-pentyltriethoxy-borate), magnesium bis(pyrenyltriethoxyborate), lithium diphenyldiethoxyborate, magnesium bis(dianthranyldi-n-butoxyborate), lithium tri(1-naphthyl)ethoxyborate, lithium triphenyl-n-butoxyborate, magnesium bis(tri(2-naphthyl)isopropoxyborate), lithium ethyltrichloroborate and lithium tri(1-naphthyl)fluoroborate.

The borate metal salt produced in the second step of the present invention by reacting lithium or magnesium or a compound containing lithium or magnesium, a halide represented by formula (4) and the boronate compound precursor obtained in the first step is presumed to be the compound represented by the following formula (9):

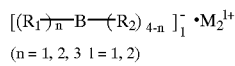
(n = 1, 2, 3  l = 1, 2)

(wherein $R_1$ and $R_2$ are the same as $R_1$ and $R_2$ in formula (1), respectively, and $M_2$ represents a lithium atom or a magnesium atom).

Specific examples of the borate metal salt represented by formula (9) include lithium ethyltributylborate, lithium phenethyltrimethylborate, lithium phenyltriisobutylborate, lithium phenethyltri(4-methylphenyl)borate, lithium ethyltriphenylborate, magnesium bis(phenethyltri(4-methylphenyl)borate), magnesium bis(n-octyltri(4,5-diethylphenyl)borate), magnesium bis(n-pentyltri(4-methoxyphenyl)borate), lithium n-butyltri(1-naphthyl)borate, magnesium bis(n-butyltri(2-naphthyl)borate), magnesium bis(n-butyltri(4-methylnaphthyl)borate), lithium n-octyltri(4,5-diethylnaphthyl)borate and magnesium bis(ethyltri-acenaphthylborate).

Specific examples of the lithium or magnesium or compound containing lithium or magnesium for use in the present invention include metallic lithium, metallic magnesium, organic or inorganic lithium compounds, and organic or inorganic magnesium compounds. Specific examples thereof include metallic lithium, metallic magnesium, methyllithium, ethyllithium, n-butyllithium, isopropylmagnesium chloride, phenylmagnesium bromide, diethylmagnesium and a combination of magnesium chloride and potassium iodide.

Specific examples of the solvent for use in the present invention include ether-type solvents such as diethyl ether, n-butylethyl ether, di-n-propyl ether, diisopropyl ether, di-n-butyl ether, 1,2-dimethoxyethane, tetrahydrofuran and 1,4-dioxane, hydrocarbon-type solvents such as hexane and cyclohexane, and aromatic solvents such as benzene, toluene and xylene. Of these, diethyl ether, tetrahydrofuran, hexane and toluene are preferred.

In the present invention, the borate compound represented by formula (1) is produced through the following first to third steps.

(First Step)

A step of producing a boronate compound precursor by:

(1) reacting lithium or magnesium or a compound containing lithium or magnesium (hereinafter referred to, if desired, as a "Li compound") with a halide represented by formula (2) [hereinafter referred to, if desired, as a "compound (2)"] in a solvent and adding thereto and reacting therewith a compound represented by formula (3) [hereinafter referred to, if desired, as a "compound (3)"];

(2) adding a reaction product of a Li compound with a compound (2) reacted in a solvent to a compound (3) to react therewith;

(3) simultaneously adding a reaction product of a Li compound with a compound (2) reacted in a solvent, and a compound (3) to react with each other; or (4) reacting a Li compound with a compound (2) in a solvent in the presence of a compound (3).

(Second Step)

A step of producing a borate metal salt by:

(5) reacting a Li compound with a halide represented by formula (4) [hereinafter referred to, if desired, as a "compound (4)"] in a solvent and adding thereto and reacting therewith a solution of the boronate compound precursor obtained in the first step;

(6) adding a reaction product of a Li compound with a compound (4) reacted in a solvent to a solution of the boronate compound precursor obtained in the first step to react therewith;

(7) simultaneously adding a reaction product of a Li compound with a compound (4) reacted in a solvent, and a solution of the boronate compound precursor obtained in the first step to react with each other; or (8) reacting a Li compound with a compound (4) in a solvent in the presence of a solution of the boronate compound precursor obtained in the first step.

(Third Step)

A step of producing a borate compound represented by formula (1) [hereinafter referred to, if desired, as a "compound (1)"] by adding an onium halide represented by formula (5) [hereinafter referred to, if desired, as a "compound (5)"] to the borate metal salt obtained in the second step to effect ion-exchange reaction.

More specifically, when metallic magnesium is used as the Li compound In the first step, the boronate compound precursor can be produced using any one of the reaction methods (1), (2), (3) and (4).

When metallic lithium or an organic lithium compound is used as the Li compound in the first step, the boronate compound precursor can be produced using any one of the reaction methods (1), (2) and (3).

When metallic magnesium is used as the Li compound in the second step, the borate metal salt can be produced using any one of the reaction methods (5), (6), (7) and (8).

When metallic lithium or an organic lithium compound is used as the Li compound in the second step, the borate metal salt can be produced using any one of the reaction methods (5), (6) and (7).

Actual procedure in the first step of the present invention is specifically described below.

An example of the reaction for producing a boronate compound precursor in the first step using metallic magnesium as the Li compound is specifically described below. In this case, the above-described reactions (1), (2), (3) and (4) are a reaction for preparing a Grignard reagent.

A small amount of an ether-type solution of compound (2) is added to metallic magnesium and the mixed solution is stirred. Then, the reaction temperature rises and reaction (Grignard reaction) starts. When the reaction is difficult to occur, iodine or methyl iodide may be added as an initiator. The reaction temperature is preferably in the vicinity of the boiling point of the solvent used and the ether-type solution of compound (2) is added such that this temperature is maintained.

For example, in the case of reaction in tetrahydrofuran, the tetrahydrofuran solution of compound (2) is preferably added such that the reaction takes place in the vicinity of from 67 to 72° C. After the ether-type solution of compound (2) is added, the mixed solution is stirred at a temperature of from room temperature to the vicinity of the boiling point of the solvent for approximately from 30 minutes to 20 hours to complete the reaction. The compound obtained is a Grignard reagent.

Then, in the case of the reaction (1), a solution of compound (3) (preferably a solution using the same solvent as the solvent in the Grignard reaction) is added to the Grignard reagent such that the reaction temperature is from $-100°$ C. to the vicinity of the boiling point of the solvent and after the addition, the reaction is allowed to proceed also at a temperature of from $-100°$ C. to the vicinity of the boiling point of the solvent for approximately from 30 minutes to 20 hours, thereby completing the first step.

In the case of the reaction (2), the Grignard reagent is added to a solution of compound (3) (preferably a solution using the same solvent as the solvent in the Grignard reaction) such that the reaction temperature is from $-100°$ C. to the vicinity of the boiling point of the solvent and after the addition, the reaction is allowed to proceed also at a temperature of from $-100°$ C. to the vicinity of the boiling point of the solvent for approximately from 30 minutes to 20 hours, thereby completing the first step.

In the case of the reaction (3), the Grignard reagent and a solution of compound (3) (preferably a solution using the same solvent as the solvent in the Grignard reaction) are simultaneously added such that the reaction temperature is from $-100°$ C. to the vicinity of the boiling point of the solvent and after the addition, the reaction is allowed to proceed also at a temperature of from $-100°$ C. to the vicinity of the boiling point of the solvent for approximately from 30 minutes to 20 hours, thereby completing the first step.

In the case of the reaction (4), a small amount of an ether-type solution of compound (2) is added to, for example, metallic magnesium and a compound (3) and the mixed solution is stirred. Then, the reaction temperature rises and the reaction starts. When the reaction is difficult to occur, iodine or methyl iodide may be added as an initiator. The reaction temperature is preferably in the vicinity of the boiling point of the solvent used and the ether-type solution of compound (2) is preferably added such that this temperature is maintained.

For example, in the case of reaction in tetrahydrofuran, the tetrahydrofuran solution of compound (2) is preferably added such that the reaction takes place in the vicinity of from 67 to 72° C. After the ether-type solution of compound (2) is added, the reaction is allowed to further proceed at a temperature of from room temperature to the vicinity of the boiling point of the solvent for approximately from 30 minutes to 20 hours, thereby completing the first step.

An example of the reaction for producing a boronate compound precursor in the first step using metallic lithium as the Li compound is specifically described below.

As described above, the boronate compound precursor can be produced using metallic lithium as the Li compound and a compound (2) according to any one of the reaction methods (1), (2) and (3). The solvent which can be used is an ether-type solvent such as diethyl ether or tetrahydrofuran, or a solvent such as hexane or cyclohexane. In this case, the reaction is generally performed in an inert gas at a temperature of from −100° C. to the vicinity of room temperature.

More specifically, a solvent described above is added to metallic lithium and thereto a solution of compound (2) is added. The reaction temperature varies depending on the compound (2) or solvent used. For example, in the case of reaction of metallic lithium with bromobenzene in diethyl ether, the diethyl ether solution of bromobenzene is preferably added such that the reaction temperature is from −78 to −70° C. After the solution of compound (2) is added, the mixed solution is stirred at a temperature of from −100° C. to the vicinity of room temperature for approximately from 30 minutes to 20 hours to prepare an organic lithium compound.

Some organic lithium compounds are commercially and easily available in the form of a solution such as hexane solution, cyclohexane solution or diethyl ether solution. In the present invention, such a commercially available organic lithium compound may be used in place of preparing an organic lithium compound as above.

Then, in the case of the reaction (1), a solution containing a compound (3) dissolved in the above-described solvent (preferably an ether-type solvent) is added to the organic lithium compound such that the reaction temperature is from −100° C. to the vicinity of room temperature. After the addition, the reaction is allowed to proceed also at a temperature of from −100° C. to the vicinity of room temperature for approximately from 30 minutes to 20 hours, thereby completing the first step.

In the case of the reaction (2), the organic lithium compound is reacted with a solution containing a compound (3) dissolved in the above-described solvent (preferably an ether-type solvent) at a reaction temperature of from −100° C. to the vicinity of room temperature for approximately from 30 minutes to 20 hours, thereby completing the first step.

In the case of the reaction (3), the organic lithium compound and a solution containing a compound (3) dissolved in the above-described solvent (preferably an ether-type solvent) are simultaneously added such that the reaction temperature is from −100° C. to the vicinity of room temperature. After the addition, the reaction is allowed to proceed also at a temperature of from −100° C. to the vicinity of room temperature for approximately from 30 minutes to 20 hours, thereby completing the first step.

An example of the reaction for producing a boronate compound precursor in the first step using an organic lithium compound as the Li compound is specifically described below.

As described above, a boronate compound precursor can be produced using an organic lithium compound as the Li compound and a compound (2) according to any one of the reaction methods (1), (2) and (3).

As the organic lithium compound, the above-described commercially available product in the form of a solution can also be used. In this case, the solvent which can be used for the reaction is an ether-type solvent such as diethyl ether or tetrahydrofuran, or a solvent such as hexane or cyclohexane.

The reaction is generally performed in an inert gas at a temperature of from −100° C. to the vicinity of room temperature. A solution of compound (2) is added to a solution of an organic lithium compound such that the reaction temperature is from −100° C. to the vicinity of room temperature to prepare an organic lithium compound. The reaction temperature varies depending on the compound (2) or solvent used. For example, in the case of reaction of n-butyllithium with 1-bromo-2,5-dimethylbenzene in diethyl ether, the diethyl ether solution of 1-bromo-2,5-dimethylbenzene is preferably added such that the reaction proceeds at from −78 to −10° C. After the solution of compound (2) is added, the mixed solution is further stirred at from −100° C. to the vicinity of room temperature for approximately from 30 minutes to 20 hours to prepare an organic lithium compound. An organic lithium compound may also be prepared by adding an organic lithium compound to the solution of compound (2) in the same conditions.

Then, in the case of the reaction (1), a solution containing a compound (3) dissolved in a solvent described above (preferably an ether-type solvent) is added to the organic lithium compound such that the reaction temperature is from −100° C. to the vicinity of room temperature and after the addition, the reaction is allowed to proceed also at a temperature of from −100° C. to the vicinity of room temperature for approximately from 30 minutes to 20 hours, thereby completing the first step.

In the case of the reaction (2), the organic lithium compound is added to a solution containing a compound (3) dissolved in a solvent described above (preferably an ether-type solvent) such that the reaction temperature is from −100° C. to the vicinity of room temperature and after the addition, the reaction is allowed to proceed also at a temperature of from −100° C. to the vicinity of room temperature for approximately from 30 minutes to 20 hours, thereby completing the first step.

In the case of the reaction (3), the organic lithium compound and a solution containing a compound (3) dissolved in a solvent described above (preferably an ether-type solvent) are simultaneously added such that the reaction temperature is from −100° C. to the vicinity of room temperature and after the addition, the reaction is allowed to proceed also at a temperature of from −100° C. to the vicinity of room temperature for approximately from 30 minutes to 20 hours, thereby completing the first step.

Actual procedure in the second step of the present invention subsequent to the first step is specifically described below.

An example of the reaction for producing a borate metal salt in the second step using metallic magnesium as the Li compound is specifically described below. In this case, the reactions (5), (6), (7) and (8) are a reaction for preparing a Grignard reagent.

A Grignard reaction is prepared in the same manner as in the preparation of a Grignard reagent from metallic magnesium and an ether-type solution of compound (2) except that an ether-type solution of compound (4) is used in place of the ether-type solution of compound (2).

Then, in the case of the reaction (5), a solution of the boronate compound precursor obtained in the first step is added to the Grignard reagent such that the reaction temperature is from $-100°$ C. to the vicinity of the boiling point of the solvent and after the addition, the reaction is allowed to proceed also at a temperature of from $-100°$ C. to the vicinity of the boiling point of the solvent for approximately from 30 minutes to 20 hours, thereby completing the second step.

In the case of the reaction (6), the Grignard reagent is added to a solution of the boronate compound precursor obtained in the first step such that the reaction temperature is from $-100°$ C. to the vicinity of the boiling point of the solvent and after the addition, the reaction is allowed to proceed also at a temperature of from $-100°$ C. to the vicinity of the boiling point of the solvent for approximately from 30 minutes to 20 hours, thereby completing the second step.

In the case of the reaction (7), the Grignard reagent and a solution of the boronate compound precursor obtained in the first step are simultaneously added such that the reaction temperature is from $-100°$ C. to the vicinity of the boiling point of the solvent and after the addition, the reaction is allowed to proceed also at a temperature of from $-100°$ C. to the vicinity of the boiling point of the solvent for approximately from 30 minutes to 20 hours, thereby completing the second step.

In the case of the reaction (8), a small amount of an ether-type solution of compound (4) is added to, for example, metallic magnesium and a solution of the boronate compound precursor obtained in the first step and the mixed solution is stirred. Then, the reaction temperature rises and the reaction starts. When the reaction is difficult to occur, iodine or methyl iodide may be added as an initiator. The reaction temperature is preferably in the vicinity of the boiling point of the solvent used and the ether-type solution of compound (4) is preferably added such that this temperature is maintained. For example, in the case of reaction in tetrahydrofuran, the tetrahydrofuran solution of compound (4) is preferably added such that the reaction takes place in the vicinity of from 67 to 72° C. After the ether-type solution of compound (4) is added, the reaction is allowed to further proceed at a temperature of from room temperature to the vicinity of the boiling point of the solvent for approximately from 30 minutes to 20 hours, thereby completing the second step.

An example of the reaction for producing a borate metal salt in the second step using metallic lithium as the Li compound is specifically described below.

As described above, the borate metal salt can be produced using metallic lithium as the Li compound and a compound (4) according to any one of the reaction methods (5), (6) and (7). The solvent which can be used is an ether-type solvent such as diethyl ether or tetrahydrofuran, or a solvent such as hexane or cyclohexane. In this case, the reaction is generally performed in an inert gas at a temperature of from $-100°$ C. to the vicinity of room temperature.

More specifically, an organic lithium compound is prepared in the same manner as in the preparation of an organic lithium compound using a solution of compound (2) except that a solvent described above is added to metallic lithium and thereto a solution of compound (4) is added in place of a solution of compound (2). A commercially available organic lithium compound may be used in place of preparing an organic lithium compound as above.

Then, in the case of the reaction (5), a solution of the boronate compound precursor obtained in the first step is added to the organic lithium compound such that the reaction temperature is from $-100°$ C. to the vicinity of room temperature. After the addition, the reaction is allowed to proceed also at a temperature of from $-100°$ C. to the vicinity of room temperature for approximately from 30 minutes to 20 hours, thereby completing the second step.

In the case of the reaction (6), the organic lithium compound is reacted with a solution of the boronate compound precursor obtained in the first step at a reaction temperature of from $-100°$ C. to the vicinity of room temperature for approximately from 30 minutes to 20 hours, thereby completing the first step.

In the case of the reaction (7), the organic lithium compound and a solution of the boronate compound obtained in the first step are simultaneously added such that the reaction temperature is from $-100°$ C. to the vicinity of room temperature. After the addition, the reaction is allowed to proceed also at a temperature of from $-100°$ C. to the vicinity of room temperature for approximately from 30 minutes to 20 hours, thereby completing the second step.

An example of the reaction for producing a borate metal salt in the second step using an organic lithium compound as the Li compound is specifically described below.

As described above, a borate metal salt can be produced using an organic lithium compound as the Li compound and a compound (4) according to any one of the reaction methods (5), (6) and (7).

The organic lithium compound is commercially and easily available in the form of a solution. In this case, the reaction solvent which can be used is an ether-type solvent such as diethyl ether or tetrahydrofuran, or a solvent such as hexane or cyclohexane.

An organic lithium compound can be prepared in the same manner as in the preparation of an organic lithium compound from a solution of an organic lithium compound (a commercially available product may also be used) and a solution of compound (2) except for using a solution of compound (4).

Then, in the case of the reaction (5), a solution of the boronate compound precursor obtained in the first step is added to the organic lithium compound such that the reaction temperature is from $-100°$ C. to the vicinity of room temperature and after the addition, the reaction is allowed to proceed also at a temperature of from $-100°$ C. to the vicinity of room temperature for approximately from 30 minutes to 20 hours, thereby completing the second step.

In the case of the reaction (6), the organic lithium compound is added to a solution of the boronate compound precursor obtained in the first step such that the reaction temperature is from $-100°$ C. to the vicinity of room temperature and after the addition, the reaction is allowed to proceed also at a temperature of from $-100°$ C. to the vicinity of room temperature for approximately from 30 minutes to 20 hours, thereby completing the second step.

In the case of the reaction (7), the organic lithium compound and a solution of the boronate compound precursor obtained in the first step are simultaneously added such that the reaction temperature is from $-100°$ C. to the vicinity of room temperature and after the addition, the reaction is allowed to proceed also at a temperature of from −100° C. to the vicinity of room temperature for approximately from 30 minutes to 20 hours, thereby completing the second step.

Actual procedure in the third step of the present invention subsequent to the second step is specifically described below.

To the reaction solution after completion of the second step, water and an appropriate organic solvent (preferably ethyl acetate or diethyl ether) are added, and the reaction product is distributed. A compound (5) is added to the aqueous phase in an amount of from 1.2 to 5 equivalent and the resulting solution is vigorously stirred so as to ion exchange the cation moiety of the borate metal salt obtained in the second step and then washed with water once or twice. Thereafter, only the organic phase is distilled off under reduced pressure and a solvent such as diethyl ether, hexane or methanol is added to the residue. The precipitate is collected by filtration and thoroughly washed with a solvent such as diethyl ether or hexane. As a result, a compound (1) can be obtained.

According to the conventional production methods, for example, in the case where the compound (1) is tetramethylammonium methyl(4-methylphenyl)borate, the production of tri(4-methylphenyl)borane is accompanied by side reaction and tetra(4-methylphenyl)borate may be by-produced to reduce the purity. However, according to the present invention, this side reaction does not occur and a high-purity borate compound can be obtained.

The present invention is described in greater detail by referring to the Examples, however, the present invention should not be construed as being limited thereto.

EXAMPLE 1

A production example of tetra-n-butylphosphonium methyltri(4-methylphenyl)borate is described below.
(First Step)

10 mg of iodine and 10 ml of diethyl ether were added to 1.00 g (41.1 mmol) of metallic magnesium and thereto, 15.0 ml (30.0 mmol) of a 2.0M diethyl ether solution of methyl bromide was added dropwise in a nitrogen atmosphere such that the reaction temperature was from −20 to −10° C. The solution was stirred at from −10 to 0° C. for 2 hours and thereto, 4.38 g (30.0 mmol) of triethyl borate was added at from −78 to −70° C. Then, the solution was further stirred at room temperature for 2 hours.
(Second Step)

30 mg of iodine and 30 ml of tetrahydrofuran were added to 3.00 g (123 mmol) of metallic magnesium and thereto, a solution containing 16.9 g (100 mmol) of 4-bromotoluene dissolved in 60 ml of tetrahydrofuran was added dropwise in a nitrogen atmosphere such that the reaction temperature was from 67 to 72° C. The resulting solution was stirred at from 30 to 50° C. for 2 hours and thereto, the reaction solution obtained in the first step was added at the same temperature. Then, the solution was further stirred at from 30 to 50° C. for 2 hours.
(Third Step)

When the reaction solution cooled to room temperature, 600 ml of diethyl ether was added thereto and then 150 ml of water was gradually added. The resulting reaction solution was transferred to a separation funnel, washed with 240 ml of water, 180 ml of a 0.2M aqueous tetra-n-butylphosphonium bromide solution and 240 ml of water in this order, and then concentrated. 600 ml of diethyl ether was added to the residue and the solid matters precipitated were collected by filtration to obtain 13.1 g (yield: 78%) of the objective compound as a white solid.

The mass spectrum of this white solid was analyzed and found that the anion moiety was 299 and the cation moiety was 259, which coincided with the theoretical values. Further, the structure of the objective compound was identified by the elemental analysis. The results are shown in Table 1.

EXAMPLE 2

A production example of tetramethylammonium n-butyltri-n-octylborate is described below.
(First Step)

To a solution containing 4.38 g (30.0 mmol) of triethyl borate dissolved in 20 ml of tetrahydrofuran, 18.8 ml (30.0 mmol) of a 1.59M hexane solution of n-butyllithium was added at from −78 to −70° C. in a nitrogen atmosphere. Then, the solution was stirred at room temperature for 2 hours.
(Second Step)

To 3.00 g (123 mmol) of metallic magnesium, a solution containing 14.7 g (100 mmol) of 1-chlorooctane dissolved in 60 ml of diethyl ether was added dropwise in a nitrogen atmosphere to prepare a Grignard reagent.

The Grignard reagent obtained was added dropwise to the reaction solution obtained in the first step such that the reaction temperature did not exceed 50° C. Then, the resulting solution was stirred at from 30 to 50° C. for 2 hours to complete the reaction.
(Third Step)

When the reaction solution cooled to room temperature, 600 ml of diethyl ether was added thereto and then 150 ml of water was gradually added. The resulting reaction solution was transferred to a separation funnel, washed with 240 ml of water, 180 ml of a 0.2M aqueous tetramethylammonium bromide solution and 240 ml of water in this order, and then concentrated. 600 ml of diethyl ether was added to the residue and the solid matters precipitated were collected by filtration to obtain 11.7 g (yield: 81%) of the objective compound as a white solid.

The mass spectrum of this white solid was analyzed and found that the anion moiety was 407 and the cation moiety was 74, which coincided with the theoretical values. Further, the structure of the objective compound was identified by the elemental analysis. The results are shown in Table 1.

EXAMPLE 3

A production example of tetra-n-butylammonium n-butyltri(4-tert-butylphenyl)borate is described below.
(First Step)

To a solution containing 4.38 g (30.0 mmol) of triethyl borate dissolved in 20 ml of tetrahydrofuran, 18.8 ml (30.0 mmol) of a 1.59M hexane solution of n-butyllithium was added at from −78 to −70° C. in a nitrogen atmosphere. Then, the solution was stirred at room temperature for 2 hours.
(Second Step)

After completion of the first step, 3.00 g (123 mmol) of metallic magnesium and 30 mg of iodine were added to the reaction solution and thereto, a solution containing 21.1 g (100 mmol) of 1-bromo-4-tert-butylbenzene dissolved in 60 ml of tetrahydrofuran was added dropwise in a nitrogen atmosphere such that the reaction temperature was from 67 to 72° C. Then, the resulting solution was stirred at from 30 to 50° C. for 2 hours to complete the reaction.
(Third Step)

When the reaction solution cooled to room temperature, 600 ml of diethyl ether was added thereto and then 150 ml of water was gradually added. The resulting reaction solution was transferred to a separation funnel, washed with 240 ml of water, 180 ml of a 0.2M aqueous tetra-n-butylammonium bromide solution and 240 ml of water in this order, and then concentrated. 600 ml of diethyl ether was added to the residue and the solid matters precipitated were collected by filtration to obtain 17.7 g (yield: 83%) of the objective compound as a white solid.

The mass spectrum of this white solid was analyzed and found that the anion moiety was 467 and the cation moiety was 242, which coincided with the theoretical values. Further, the structure of the objective compound was identified by the elemental analysis. The results are shown in Table 1.

EXAMPLE 4

A production example of tetra-n-butylammonium n-butyltri(4-methyl-1-naphthyl)borate is described below.
(First Step)

10 mg of iodine and 10 ml of tetrahydrofuran were added to 1.00 g (41.1 mmol) of metallic magnesium and thereto, a solution containing 4.11 g (30 mmol) of n-butyl bromide dissolved in 20 ml of tetrahydrofuran was added dropwise in a nitrogen atmosphere such that the reaction temperature was 67 to 72° C. Then, the solution was stirred at room temperature for 2 hours and thereto, 4.38 g (30.0 mmol) of triethyl borate was added at from −78 to −70° C., followed by further stirring at room temperature for 2 hours.
(Second Step)

After completion of the first step, 3.00 g (123 mmol) of metallic magnesium and 30 mg of iodine were added to the reaction solution and thereto, a solution containing 22.1 g (100 mmol) of 1-bromo-4-methylnaphthalene dissolved in 60 ml of tetrahydrofuran was added dropwise in a nitrogen atmosphere such that the reaction temperature was from 67 to 72° C. Then, the resulting solution was stirred at from 30 to 50° C. for 2 hours to complete the reaction.
(Third Step)

When the reaction solution cooled to room temperature, 600 ml of ethyl acetate was added thereto and then 150 ml of water was gradually added. The resulting reaction solution was transferred to a separation funnel, washed with 240 ml of water, 180 ml of a 0.2M aqueous tetra-n-butylammonium bromide solution and 240 ml of water in this order, and then concentrated. 600 ml of diethyl ether was added to the residue and the solid matters precipitated were collected by filtration to obtain 17.0 g (yield: 77%) of the objective compound as a white solid.

The mass spectrum of this compound was analyzed and found that the anion moiety was 491 and the cation moiety was 242, which coincided with the theoretical values. Further, the structure of the objective compound was identified by the elemental analysis. The results are shown in Table 1.

EXAMPLE 5

A production example of tetra-n-butylammonium n-butyltri(4-methyl-1-naphthyl)borate is described below.
(First Step)

10 mg of iodine, 4.38 g (30.0 mmol) of triethyl borate and 10 ml of tetrahydrofuran were added to 4.00 g (164 mmol) of metallic magnesium and thereto, a solution containing 19.9 g (90 mmol) of 1-bromo-4-methylnaphthalene dissolved in 60 ml of tetrahydrofuran was added dropwise in a nitrogen atmosphere such that the reaction temperature was 67 to 72° C. Then, the solution was stirred at from 30 to 50° C. for 2 hours.

(Second Step)

After completion of the first step, 10 mg of iodine was added to the reaction solution and thereto, a solution containing 4.11 g (30 mmol) of n-butyl bromide dissolved in 20 ml of tetrahydrofuran was added dropwise in a nitrogen atmosphere such that the reaction temperature was from 67 to 72° C. Then, the resulting solution was stirred at from 30 to 50° C. for 2 hours to complete the reaction.
(Third Step)

When the reaction solution cooled to room temperature, 600 ml of ethyl acetate was added thereto and then 150 ml of water was gradually added. The resulting reaction solution was transferred to a separation funnel, washed with 240 ml of water, 180 ml of a 0.2M aqueous tetra-n-butylammonium bromide solution and 240 ml of water in this order, and then concentrated. 600 ml of diethyl ether was added to the residue and the solid matters precipitated were collected by filtration to obtain 17.7 g (yield: 80%) of the objective compound as a white solid.

The mass spectrum of this compound was analyzed and found that the anion moiety was 491 and the cation moiety was 242, which coincided with the theoretical values. Further, the structure of the objective compound was identified by the elemental analysis. The results are shown in Table 1.

EXAMPLE 6

A production example of tetra-n-butylammonium n-butyltri(4-methyl-1-naphthyl)borate is described below.
(First Step)

10 mg of iodine, 30.0 ml (30.0 mmol) of a 1.0M boron trichloride hexane solution and 10 ml of tetrahydrofuran were added to 4.00 g (164 mmol) of metallic magnesium and thereto, a solution containing 19.9 g (90 mmol) of 1-bromo-4-methylnaphthalene dissolved in 60 ml of tetrahydrofuran was added dropwise in a nitrogen atmosphere such that the reaction temperature was 67 to 72° C. Then, the solution was stirred at from 30 to 50° C. for 2 hours.
(Second Step)

After completion of the first step, 10 mg of iodine was added to the reaction solution and thereto, a solution containing 4.11 g (30 mmol) of n-butyl bromide dissolved in 20 ml of tetrahydrofuran was added dropwise in a nitrogen atmosphere such that the reaction temperature was from 67 to 72° C. Then, the resulting solution was stirred at from 30 to 50° C. for 2 hours to complete the reaction.
(Third Step)

When the reaction solution cooled to room temperature, 600 ml of ethyl acetate was added thereto and then 150 ml of water was gradually added. The resulting reaction solution was transferred to a separation funnel, washed with 240 ml of water, 180 ml of a 0.2M aqueous tetra-n-butylammonium bromide solution and 240 ml of water in this order, and then concentrated. 600 ml of diethyl ether was added to the residue and the solid matters precipitated were collected by filtration to obtain 16.5 g (yield: 75%) of the objective compound as a white solid.

The mass spectrum of this compound was analyzed and found that the anion moiety was 491 and the cation moiety was 242, which coincided with the theoretical values. Further, the structure of the objective compound was identified by the elemental analysis. The results are shown in Table 1.

EXAMPLE 7

A production example of tetraethylammonium phenyltri (2,5-dimethylphenyl)borate is described below.

(First Step)

10 mg of iodine and 10 ml of tetrahydrofuran were added to 1.00 g (41.1 mmol) of metallic magnesium and thereto, a solution containing 4.71 g (30.0 mmol) of phenyl bromide dissolved in 20 ml of tetrahydrofuran was added dropwise in a nitrogen atmosphere such that the reaction temperature was 68 to 72° C. Then, the solution was stirred at from 30 to 50° C. for 2 hours to prepare a Grignard reagent.

The Grignard reagent obtained was added to a solution containing 4.38 g (30.0 mmol) of triethyl borate dissolved in 20 ml of tetrahydrofuran at from −78 to 70° C. and the resulting solution was stirred at room temperature for 2 hours.

(Second Step)

30 ml of diethyl ether was added to 0.9 g (129 mmol) of metallic lithium and thereto, a solution containing 18.3 g (100 mmol) of 1-bromo-2,5-dimethylbenzene dissolved in 60 ml of diethyl ether was added dropwise in a nitrogen atmosphere such that the reaction temperature was −75 to −65° C. The resulting solution was stirred at the same temperature for 2 hours and added dropwise to the reaction solution obtained after completion of the first step such that the reaction temperature did not exceed 5° C. Then, the resulting solution was further stirred at from 0 to 5° C. for 2 hours to complete the reaction.

(Third Step)

When the reaction solution warmed to room temperature, 600 ml of diethyl ether was added thereto and then 150 ml of water was gradually added. The resulting reaction solution was transferred to a separation funnel, washed with 240 ml of water, 180 ml of a 0.2M aqueous tetraethylammonium bromide solution and 240 ml of water in this order, and then concentrated. 600 ml of diethyl ether was added to the residue and the solid matters precipitated were collected by filtration to obtain 10.2 g (yield: 64%) of the objective compound as a white solid.

The mass spectrum of this compound was analyzed and found that the anion moiety was 403 and the cation moiety was 130, which coincided with the theoretical values. Further, the structure of the objective compound was identified by the elemental analysis. The results are shown in Table 1.

EXAMPLE 8

A production example of tetra-n-butylammonium n-butyltri(4-tert-butylphenyl)borate is described below.

(First Step)

To a solution containing 4.74 g (30.0 mmol) of 2-butoxy-1,3,2-dioxaborinane dissolved in 20 ml of tetrahydrofuran, 18.8 ml (30.0 mmol) of a 1.59M hexane solution of n-butyl lithium was added in a nitrogen atmosphere at from −78 to −70° C. and then, the solution was stirred at room temperature for 2 hours.

(Second Step)

To the reaction solution after completion of the first step, 3.00 g (123 mmol) of metallic magnesium and 30 mg of iodine were added and thereto a solution containing 21.1 g (100 mmol) of 1-bromo-4-tert-butylbenzene dissolved in 60 ml of tetrahydrofuran was added dropwise in a nitrogen atmosphere such that the reaction temperature was from 67 to 72° C. The resulting solution was further stirred at from 30 to 50° C. for 2 hours to complete the reaction.

(Third Step)

After the reaction solution cooled to room temperature, 600 ml of diethyl ether was added thereto and then 150 ml of water was gradually added. The resulting reaction solution was transferred to a separation funnel, washed with 240 ml of water, 180 ml of a 0.2M aqueous tetra-n-butylammonium bromide solution and 240 ml of water in this order, and then concentrated. 600 ml of diethyl ether was added to the residue and the solid matters precipitated were collected by filtration to obtain 17.3 g (yield: 81%) of the objective compound as a white solid.

The mass spectrum of this compound was analyzed and found that the anion moiety was 467 and the cation moiety was 242, which coincided with the theoretical values. Further, the structure of the objective compound was identified by the elemental analysis. The results are shown Table 1.

TABLE 1

Results of Elemental Analysis

| Example | | C | H | N | B | P |
|---|---|---|---|---|---|---|
| 1 | Calculated | 81.70 | 10.82 | — | 1.94 | 5.54 |
|   | Found | 83.12 | 10.33 | — | 1.97 | 5.42 |
| 2 | Calculated | 79.78 | 15.06 | 2.91 | 2.24 | — |
|   | Found | 79.70 | 15.08 | 2.82 | 2.39 | — |
| 3 | Calculated | 84.58 | 11.92 | 1.97 | 1.52 | — |
|   | Found | 84.69 | 11.87 | 1.85 | 1.59 | — |
| 4 | Calculated | 86.73 | 9.89 | 1.91 | 1.47 | — |
|   | Found | 86.99 | 9.53 | 2.10 | 1.38 | — |
| 5 | Calculated | 86.73 | 9.89 | 1.91 | 1.47 | — |
|   | Found | 86.80 | 9.69 | 1.79 | 1.72 | — |
| 6 | Calculated | 86.73 | 9.89 | 1.91 | 1.47 | — |
|   | Found | 86.96 | 9.92 | 1.70 | 1.42 | — |
| 7 | Calculated | 85.53 | 9.82 | 2.62 | 2.03 | — |
|   | Found | 85.49 | 9.95 | 2.55 | 2.00 | — |
| 8 | Calculated | 84.58 | 11.92 | 1.97 | 1.52 | — |
|   | Found | 84.51 | 11.85 | 1.87 | 1.55 | — |

According to the production method of borate compounds of the present invention, a high-purity borate compound useful as a photoinitiator or photoabsorptive decolorizer can be obtained in a high yield as compared with conventional production methods.

While the invention has been described in detail and with reference to specific examples thereof, it will be apparent to one skilled in the art that various changes and modifications can be made therein without departing from the spirit and scope thereof.

What is claimed is:

1. A method for producing a borate compound represented by formula (1), comprising:
    a first step of reacting lithium or magnesium or a compound containing lithium or magnesium, a halide represented by formula (2) and a compound represented by formula (3) in a solvent to produce a boronate compound precursor;
    a second step of reacting lithium or magnesium or a compound containing lithium or magnesium, a halide represented by formula (4) and the boronate compound precursor obtained in the first step in a solvent to produce a borate metal salt; and
    a third step of adding an onium halide represented by formula (5) to the borate metal salt obtained in the second step to effect ion-exchange reaction:

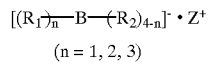

(1)

$(n = 1, 2, 3)$ (wherein $R_1$ and $R_2$ are different from each other and $R_1$ and $R_2$ each independently represents an alkyl group, an alkenyl group, an aryl group, an aralkyl group, a heterocyclic group or an alicyclic group, and $Z^+$ represents an ammonium cation, a sulfonium cation, an oxosulfonium cation, a pyridinium cation, a phosphonium cation or an iodonium cation);

$$R_1\text{—}Y_1 \qquad (2)$$

(wherein $R_1$ is the same as $R_1$ in formula (1), and $Y_1$ represents a halogen atom);

$$R_3\text{—}B\begin{matrix}R_4\\R_5\end{matrix} \qquad (3)$$

(wherein $R_3$, $R_4$ and $R_5$, which may be the same or different, each represents an alkyloxy group, an alkenyloxy group, an aryloxy group, an aralkyloxy group or a halogen atom and when $R_4$ and $R_5$ are an alkyloxy group, an alkenyloxy group, an aryloxy group or an aralkyloxy group, $R_4$ and $R_5$ may be combined to each other to form a cyclic structure together with the boron atom);

$$R_2\text{—}Y_2 \qquad (4)$$

(wherein $R_2$ is the same as $R_2$ in formula (1), and $Y_2$ represents a halogen atom);

$$Z^+ \cdot X^- \qquad (5)$$

(wherein $Z^+$ is the same as $Z^+$ in formula (1), and X represents a halogen atom).

2. The method for producing a borate compound as claimed in claim 1, wherein in the first step, the boronate compound precursor is produced by:

(A) reacting lithium or magnesium or a compound containing lithium or magnesium with a halide represented by formula (2) in a solvent and adding thereto and reacting therewith a compound represented by formula (3);

(B) adding a reaction product of lithium or magnesium or a compound containing lithium or magnesium with a halide represented by formula (2) reacted in a solvent to a compound represented by formula (3) to react therewith;

(C) simultaneously adding a reaction product of lithium or magnesium or a compound containing lithium or magnesium with a halide represented by formula (2) reacted in a solvent, and a compound represented by formula (3) to react with each other; or (D) reacting lithium or magnesium or a compound containing lithium or magnesium with a halide represented by formula (2) in a solvent in the presence of a compound represented by formula (3).

3. The method for producing a borate compound as claimed in claim 1, wherein in the second step, the borate metal salt is produced by:

(E) reacting lithium or magnesium or a compound containing lithium or magnesium with a halide represented by formula (4) and adding thereto and reacting therewith the boronate compound precursor obtained in the first step;

(F) adding a reaction product of lithium or magnesium or a compound containing lithium or magnesium with a halide represented by formula (4) reacted in a solvent to the boronate compound precursor obtained in the first step to react therewith;

(G) simultaneously adding a reaction product of lithium or magnesium or a compound containing lithium or magnesium with a halide represented by formula (4) reacted in a solvent, and the boronate compound precursor obtained in the first step to react with each other; or (H) reacting lithium or magnesium or a compound containing lithium or magnesium with a halide represented by formula (4) in a solvent in the presence of the boronate compound precursor obtained in the first step.

4. The method for producing a borate compound as claimed in claim 1, wherein the lithium or magnesium or compound containing lithium or magnesium used in the first step is metallic lithium, metallic magnesium or an organic lithium compound.

5. The method for producing a borate compound as claimed in claim 1, wherein the lithium or magnesium or compound containing lithium or magnesium used in the second step is metallic lithium, metallic magnesium or an organic lithium compound.

6. The method for producing a borate compound as claimed in claim 1, wherein the first step and the second step are continuously performed in the same reaction vessel.

7. The method for producing a borate compound as claimed in claim 6, wherein the lithium or magnesium or compound containing lithium or magnesium used in the first step and the second step is metallic magnesium and the metallic magnesium for use in the second step is added simultaneously with the metallic magnesium for use in the first step.

8. The method for producing a borate compound as claimed in claim 1, wherein the compound represented by formula (3) used in the first step is trialkyl borate.

9. The method for producing a borate compound as claimed in claim 1, wherein the solvent used in the second step is tetrahydrofuran.

10. The method for producing a borate compound as claimed in claim 1, wherein the halide represented by formula (2) used in the first step is a halide where $R_1$ is an α-naphthyl group which may have a substituent or a β-naphthyl group which may have a substituent.

* * * * *